(12) United States Patent
Kalkum et al.

(10) Patent No.: US 7,105,357 B1
(45) Date of Patent: Sep. 12, 2006

(54) METHOD AND DEVICE FOR PROCESSING EXTREMELY SMALL SUBSTANCE QUANTITIES

(75) Inventors: Markus Kalkum, New York, NY (US); Martin Müller, Berlin (DE); Eckhardt Nordhoff, Berlin (DE); Holger Eickhoff, Berlin (DE); Holger Rauth, Berlin (DE); Richard Reinhardt, Berlin (DE)

(73) Assignee: Max-Planck-Gesellschaft zur Forderung der Wissenschaften e. V., (DE)

( * ) Notice: Subject to any disclaimer, the term of this patent is extended or adjusted under 35 U.S.C. 154(b) by 0 days.

(21) Appl. No.: 09/701,203

(22) PCT Filed: May 27, 1999

(86) PCT No.: PCT/EP99/03667

§ 371 (c)(1),
(2), (4) Date: Jan. 12, 2001

(87) PCT Pub. No.: WO99/61881

PCT Pub. Date: Dec. 2, 1999

(30) Foreign Application Priority Data

May 27, 1998 (DE) ................... 198 23 719

(51) Int. Cl.
*G01N 1/10* (2006.01)
*G01N 35/553* (2006.01)
*B01L 3/02* (2006.01)
*B01L 11/00* (2006.01)

(52) U.S. Cl. .............. 436/180; 422/100; 422/101; 436/526

(58) Field of Classification Search ............... 422/100, 422/101, 99, 103–105; 436/180, 526; 73/863.32, 73/864, 864.01, 864.11
See application file for complete search history.

(56) References Cited

U.S. PATENT DOCUMENTS

| 3,985,649 | A | | 10/1976 | Eddelman | |
|---|---|---|---|---|---|
| 5,147,529 | A | | 9/1992 | Lee et al. | |
| 5,186,827 | A | | 2/1993 | Liberti et al. | |
| 5,482,863 | A | * | 1/1996 | Knobel | 436/54 |
| 5,482,864 | A | * | 1/1996 | Knobel | 436/54 |
| 5,498,550 | A | | 3/1996 | Fujiwara et al. | |
| 5,567,326 | A | | 10/1996 | Ekenberg et al. | |
| 5,702,950 | A | * | 12/1997 | Tajima | 436/49 |
| 5,705,062 | A | * | 1/1998 | Knobel | 210/205 |
| 5,895,631 | A | * | 4/1999 | Tajima | 422/101 |
| 5,916,524 | A | * | 6/1999 | Tisone | 422/100 |
| 5,976,369 | A | * | 11/1999 | Howe et al. | 210/222 |
| 6,083,762 | A | * | 7/2000 | Papen et al. | 436/180 |
| 6,096,554 | A | * | 8/2000 | Tajima | 436/49 |
| 6,133,037 | A | * | 10/2000 | Tajima | 436/49 |
| 6,135,325 | A | * | 10/2000 | Fessel et al. | 222/309 |

(Continued)

FOREIGN PATENT DOCUMENTS

JP        08/062224        3/1996

(Continued)

*Primary Examiner*—Brian R. Gordon
(74) *Attorney, Agent, or Firm*—DLA Piper Rudnick Gray Cary US LLP

(57) ABSTRACT

For processing of substances in the reservoir (3) of a microdroplet dosing device (1), movement of a solid carrier material with a binding-active surface takes place in the reservoir, and binding of the substance takes place on the surface of the carrier material which comprises magnetic particles (7) or a carrier pad.

11 Claims, 2 Drawing Sheets

U.S. PATENT DOCUMENTS

| | | |
|---|---|---|
| 6,187,270 B1 * | 2/2001 | Schmitt et al. .............. 422/101 |
| 6,207,463 B1 * | 3/2001 | Tuunanen ................... 436/526 |
| 6,231,814 B1 * | 5/2001 | Tajima ....................... 422/101 |
| 6,331,277 B1 * | 12/2001 | Tajima ....................... 422/100 |
| 6,448,092 B1 * | 9/2002 | Tuunanen ................... 436/526 |
| 6,455,325 B1 * | 9/2002 | Tajima ....................... 436/526 |
| 6,468,810 B1 * | 10/2002 | Korpela ...................... 436/526 |
| 6,509,193 B1 * | 1/2003 | Tajima ......................... 436/49 |
| 6,764,859 B1 * | 7/2004 | Kreuwel et al. ............ 436/178 |
| 6,942,806 B1 * | 9/2005 | Franzreb et al. ............ 210/695 |
| 2001/0007770 A1 * | 7/2001 | Tajima ......................... 436/47 |
| 2005/0013741 A1 * | 1/2005 | a'Brassard ................... 422/99 |

FOREIGN PATENT DOCUMENTS

| | | |
|---|---|---|
| WO | WO 86/06493 | 11/1986 |
| WO | WO 89/01161 | 2/1989 |
| WO | WO 96/09550 | 3/1996 |
| WO | WO 97/31105 | 8/1997 |
| WO | WO 97/44134 | 11/1997 |
| WO | WO 97/44671 | 11/1997 |

* cited by examiner

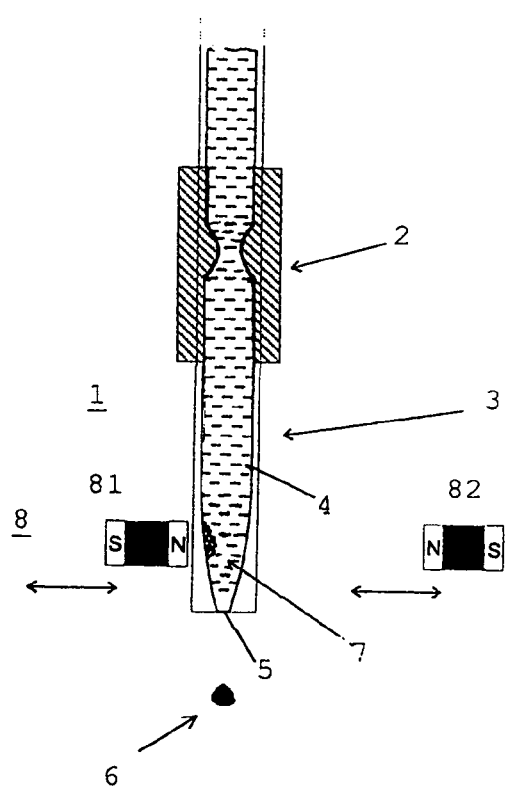
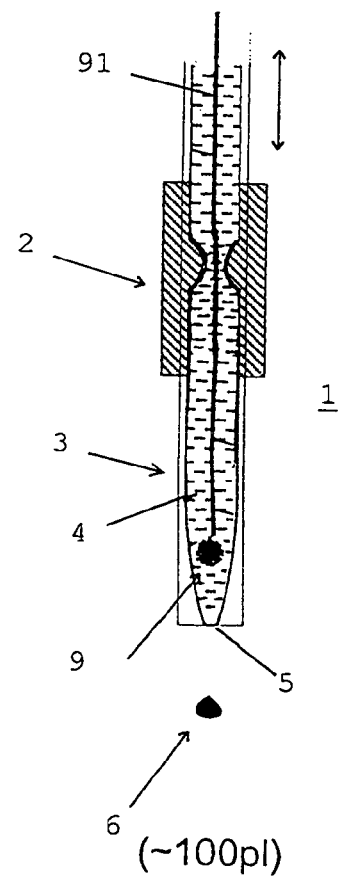
Fig. 1
Fig. 2

METHOD AND DEVICE FOR PROCESSING EXTREMELY SMALL SUBSTANCE QUANTITIES

FIELD OF THE INVENTION

The invention relates to a method for processing extremely small substance quantities in the reservoir of a liquid-dosing device, in particular to a method for collecting, purifying and/or concentrating substance samples in capillary vessels, e.g. in micropipettes or microdispensers, as well as devices for implementing the method.

BACKGROUND

In the field of biochemistry, gene technology and medicine, minute sample quantities are obtained, detected, analysed, handled or processed. Often the tasks consist of transferring the samples which are dissolved or suspended in a liquid, between macroscopic receptacles such as e.g. micro titre plates (µl volumes) and miniaturised carriers such as e.g. membranes, filters MALDI-MS targets, silicon wafers or nano titre plates (nl volumes). Tools known for transferring minimum substance quantities (lower limit approx. 1/10 nl) are so-called pin tools where the samples to be transferred adhere to needle points, or micropipettes or microdispensers where, analogous to inkjet printing technology applications, minute droplets with the incorporated sample are placed on the respective target substrate. Transfer at the interface between macroscopic receptacles and miniaturised carriers is generally associated with the problem that as a result of using part of the sample quantity present in the macroscopic receptacle, after transfer to the miniaturised carrier the quantity of substance present is insufficient to undertake a reliable analysis or treatment step. For this reason there is an interest in concentrating, collecting and/or purifying substance quantities in small volumes (µl range).

In the detection of substances of interest, mass-spectrometry processes nowadays achieve detection sensitivities in the attomol to lower femtomol region. Such sensitivity can effectively be used in practice only if the analyte is present in as pure a form as possible, at a volume comprising only a few nanolitres. For this purpose too, there is an interest in purifying or enriching substance samples.

From chemical and biochemical analysis it is generally known for sample enrichment to introduce solid phases in the respective solution or suspension, to which solid phases the desired molecules can temporarily be bound. With suitable magnetic materials properties, the solid phases can be manipulated under the influence of magnetic field forces (magnetic purification).

From U.S. Pat. No. 5,186,827, a magnetic separation device for separating magnetic particles from a non-magnetic test medium is known. The magnetic particles are small particles to whose surfaces the substances of interest are bound, or for example biological cells into which magnetic substances have been incorporated. With the use of a multitude of magnets, a magnetic field gradient is established in the test medium such that the magnetic particles are moved to the walls of the vessel where they are collected. The magnetic separation device known from U.S. Pat. No. 5,186,872 has the following disadvantages.

The design of the separation device is complex. To form the field gradients, at least four magnets are required which have to be arranged in a predetermined way and which require the use of particular receptacles for the test medium. In particular when electromagnets are used, the conventional separation device, which has been designed for characteristic receptacle dimensions in the cm region, does not allow miniaturisation. This precludes its use on the above-mentioned interface between macroscopic receptacles and miniature carriers with the tools used. Moreover, the conventional separation device is limited to separation only. There is no provision for loading magnetic particles with the substances of interest in the separation device.

From U.S. Pat. No. 5,498,550 a sample collector is known in which complexes of protein samples and magnetically marked antibodies are manipulated in a reactor under the influence of an external magnetic field. However, this sample collector is not suitable for handling substance quantities with volumes in the nl to µl range. A further disadvantage is that the respective antigen-antibody reaction for complex formation is limited to particular substances. Furthermore, a system for controlling magnetic particles in pipetting arrangements is known from WO 97/44671 and JP 08/062,224 (in: Patent Abstracts of Japan, 1996). The magnetic particles are suspended in a pipette-shaped cell; they can be pulled to the rim of the cell using an external permanent magnet. When the permanent magnet is removed, the particles are released and can therefore sink to the lower end of the cell which is open. But this system too is limited to manipulation of larger sample volumes in the ml range. Furthermore there is an advantage in that particle control only comprises binding or release, but not targeted movement of the particles in the cell. A magnetic separation device is described in WO 96/09550 (or U.S. Pat. No. 5,567,326) in which magnetisable particles are extracted from a non-magnetic test medium. The test medium is accommodated in a cell arrangement in which each cell is adapted for immersing a pin-shaped permanent magnet. This technology is associated with the disadvantage that the cells do not allow any dispersing of the test medium and that consequently the test medium is difficult to handle.

Further systems for manipulating magnetic or magnetisable particles are known from WO 86/06493, WO 89/01161, U.S. Pat. No. 5,147,529 and U.S. Pat. No. 3,985,649. However, none of these systems allow delivery of media in the same way as a dispenser. However, this dispensing function is of decisive importance in particular in the context of the tasks in biochemistry, gene technology and medicine mentioned above.

From WO 97/31105 a method for treating biopolymers, micro-organisms or materials with several types of magnetic particles is known. The materials to be treated are placed in a reservoir with the magnetic particles and bound to their surfaces. With a pipette, samples are taken from the supply vessel. Under the influence of a magnetic field, magnetic particles with bound materials can be held fast in the inside of the pipette. From WO 97/44134, a droplet shot device is known with which microscopic liquid droplets can be transferred to substrates.

At present, no purification or enrichment technology is known which can be used for processing (e.g. handling, collecting, purifying or similar) extremely small substance quantities (down to the nl range and below).

It is accordingly an object of the invention to provide a method for processing extremely small substance quantities which in particular is compatible with the use of traditional tools for handling samples in the nl-range and which has the widest possible scope of application. The method is to be easy to integrate into the conventional methods for handling samples, for detecting samples and for processing samples from biochemistry, gene technology and medicine. It is also the object of the invention to provide a device for implementing such a method.

SUMMARY OF THE INVENTION

The method according to the invention, for collecting substance samples is based on the arrangement and movement of a solid phase (carrier material) directly in the reservoir of a microdosing device, with the substance of interest being bound on the surface of the carrier material and held in the reservoir for a predetermined sequence of work steps. The reservoir has a characteristic volume which is generally less than 500 µl and preferably less than 10 µl, in particular less than 2 µl, to 1 nl. The dosing device is designed for microdroplet delivery in the sub-nl range. The carrier material can be constituted by magnetic particles which are moved by an exterior magnetic field force or by a porous carrier pad which is moved by exterior mechanical activation. The carrier material comprises an incompressible and hard material. This means that when the dosing device is activated, e.g. by applying a pressure pulse, the form of the carrier material does not change.

Binding between the substance or substances of interest and the surface of the carrier material takes place by means of van-der-Vaals forces due to hydrophobic interactions. This means that binding takes place at a relatively low specificity concerning the individual material, and thus that the invention can be implemented with entire substance classes in materials mixtures (e.g. mixtures of peptides, proteins, DNA or oligonucleotides).

The term "reservoir" of the dosing device refers to the active dosing volume or stroke volume or, in the case of implementation with respective devices, the pipette volume or dispenser volume. The dosing device can be constituted by any suitable pumping device or dosing device which can deliver predetermined quantities of liquid from the reservoir to a target substrate. Preferably, the invention is implemented with dosing devices for extremely small substance quantities (nanolitre and sub-nanolitre). This includes for example micropipettes or microdispensers or micropumps (in particular with pneumatic or electric drive) or other micro droplet delivery devices which work analogously to inkjet printer techniques.

For processing extremely small substance quantities, the carrier material is preferably arranged or moved in close proximity of an exit aperture of the reservoir of the dosing device. This involves for example manipulation of the carrier material at or near the tip of a dosing capillary, e.g. a microdispenser. The invention provides a particular advantage in that it is compatible with any conventional dosing device. It has been found for the first time that sample collection according to the principle of solid-phase purification (which is known per se) is possible in dosing devices without impairing the function of said dosing devices. This applies in particular to the implementation of the invention in microdosing devices with nl volumes.

A device according to the invention is characterised in that in the reservoir of a liquid dosing device, a carrier means is arranged as a solid phase with binding-active surface, and able to be manipulated by an exterior drive device. Preferably, a multitude of liquid dosing devices are operated in parallel, with only one common drive device for manipulation of the solid phases being provided.

The invention has the advantage in that for the first time the problem of miniaturised sample purification or sample collection is solved. The invention can be implemented simply with available micropipettes or microdispensers, in particular if they are used individually or serially, without interfering with any conventional process steps. It has become possible for the first time to bind sample substances in microdispensers to a carrier material and to move said sample systems in said microdispenser, without limiting the function of the microdispenser. This represents an unexpected and significant success since normally, e.g. piezoelectric microdispensers do not function if a compressible component, e.g. based on particles, suspended liquids or gas inclusions is present in their interior. It has been shown that when magnetic particles with a characteristic size ranging from 200 nm to 1 µm are used as a carrier material, in an advantageous way a dual function is fulfilled. On the one hand they have a very large affine surface for binding the sample substances. On the other hand the dispensing process is not disturbed by the small particles, with in particular blocking of the outlet nozzle also being precluded. The invention allows both the binding of the substances of interest to the carrier material and its manipulation within a receptacle of the reservoir without any additional steps. Such manipulation in particular comprises elution of the substances phase-bound to the carrier material.

A particular advantage of the invention concerns its use with micropipettes or microdispensers. For reproducible exact dispensing of extremely small quantities of liquids, the geometric characteristics of the dispenser tip and the electrical piezo parameters must be optimally attuned to each other. The invention makes it possible that the solid carrier material required for temporary binding of the molecules does not interfere with the dispersing process, i.e. that neither the receptacle dimensions nor the pressure wave travelling through the liquid are effectively influenced.

BRIEF DESCRIPTION OF THE DRAWINGS

Further advantages and details of the invention are described below, referring to the enclosed drawings:

FIG. 1 is a diagrammatic illustration of a first embodiment of the invention, in which a magnetic carrier material is used in a dosing device;

FIG. 2 is a diagrammatic illustration of a second embodiment of the invention in which a porous carrier pad is used in a dosing device;

DETAILED DESCRIPTION

Figure 3:
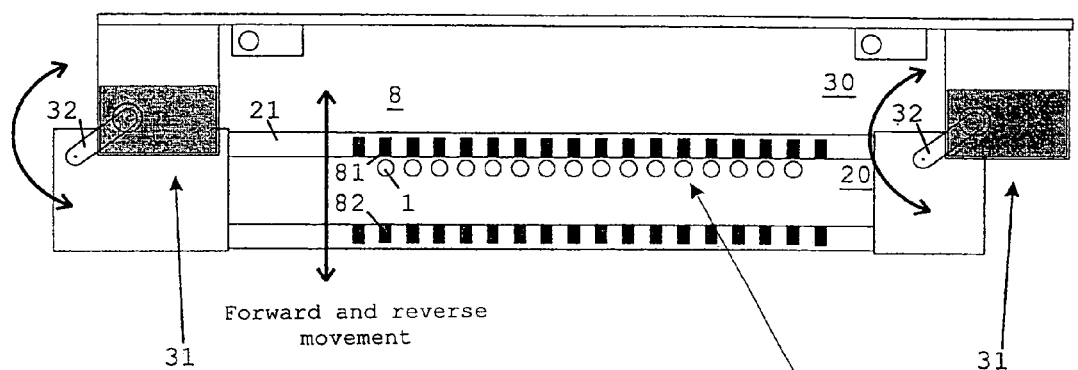
FIG. 3 is a diagrammatic top view of a device according to the invention with a series of microdispensers which are adapted for implementing the method according to the invention.

The invention is preferably implemented with dosing devices which are adapted to deliver liquid quantities in the nl to pl range. This means that the dosing device comprises a dosing reservoir in the 1/10 nl to µl range, said dosing reservoir being able to deliver droplets or portions with a volume below 100 pl, preferably by pressure activation. An example of such a dosing device is a microdispenser explained below with reference to FIGS. 1 and 2.

By way of example, FIG. 1 shows the end of a piezoelectric microdispenser adapted for implementing the method according to the invention according to a first embodiment of the invention (magnetic manipulation of the solid carrier material). The piezoelectric dispenser 1 comprises an electrical transducer 2 and a dosing reservoir 3 formed by a capillary. The transducer 2 is adapted for pulse-shaped reduction of the volume of the dosing reservoir 3. When activating the transducer 2 for a pulse time (typically approx. 40 µs) a pressure wave travels through the liquid 4 in the dosing reservoir 3. This results in liquid being ejected at the outlet 5 (diameter approx. 50 µm) of the dosing reservoir 3, said outlet 5 being formed by the end of the capillary (tip of the dispenser). When the pressure wave in the liquid 4 overcomes the retention forces (capillary forces and surface tension) occurring at the outlet 5, a droplet 6 is delivered.

The liquid 4 for example comprises a solution or suspension of sample molecules which in the case of biochemical applications comprise peptides, proteins, nucleic acids or DNA molecules, fats or carbohydrates. So as to concentrate or purify according to the invention the sample molecules (substance sample) in the dosing reservoir 3, a multitude of magnetic particles 7 is arranged in the dosing reservoir 3, preferably near the outlet 5, said magnetic particles 7 being able to be manipulated by means of a drive device in the form of a magnet device 8 for holding and/or moving the magnetic particles 7. The magnet device 8 comprises two permanent magnets 81, 82, each with adjustable spacing in relation to the dosing reservoir 3 with the magnetic particles. Both permanent magnets 81, 82 point with the same pole towards reservoir 3. Further details of the magnet device 8 and an associated drive device (not shown) are explained below with reference to FIGS. 3 and 4.

The diameter of the magnetic particles 7 is approximately one to two powers of ten smaller than the diameter of the dispenser nozzle (outlet 5), preferably ranging between 0.25 and 2 µm. This ensures that the particles 7 can easily be taken up, by suction, as a suspension into the dispenser 1 and deposited or moved in the dosing reservoir 3. This is even possible near the outlet 5, because the magnetic field influence of the magnet device 8 advantageously prevents particles 7 reaching outlet 5 or moving beyond said outlet 5. The particle size stated provides a further advantage in that the deposited particles 7, i.e. the particles adhering to the inner wall of the dispenser as a result of the magnetic field force, due to their small volume do not impede the piezoelectric dispensing process. Preferably, commercially available substances of sufficient magnetisability and with the largest possible active particle surface are used as magnetic particles 7. The particles 7 have an affinity to the sample molecules so that said sample molecules in the liquid 4 are bound to the particles in the interior of the dispenser tip.

According to the invention the magnetic particles 7 can be moved in a predefined way in the dosing reservoir 3. The change of magnetic field forces takes place by a movement of the microdispenser 1 and the magnet device 8 relative to each other, with preferably the permanent magnets 81, 82 being moved in relation to the stationary dispenser tip. It is thus for example possible by simultaneously moving magnet 81 further away while moving magnet 82 closer from the opposite dispenser side, to move the particles with the sample load through the liquid 4 from one wall of the dosing reservoir 3 to the opposite wall. The particles 7 which form the solid carrier material (solid phase) are moved through the liquid, establish contact with the surrounding flowing liquid and are mixed with the liquid so that further sample molecules are bound while other components of the solution remain in the liquid 4. By repeated movement of the particles 7 through the liquid 4, adequate quantities of interesting sample molecules can be collected (enrichment). Aimed movement of the particles with the bound sample substances through the liquid represents a significant advantage of the invention which cannot be achieved by traditional dispensing systems with large volumes of liquid. According to the invention, not only statically-bound or released states are decisive in relation to the particles, but also dynamically-bound states in which targeted movement through the liquid takes place. Further processing steps are explained below.

The permanent magnets 81, 82 are preferably NdFeB-magnets with a remanence selected according to the application. For use with microdispensers, the remanence is preferably approx. 1 Tesla to 1.5 Tesla.

FIG. 2 shows a second embodiment of the invention again using the example of a microdispenser 1 with a piezoelectric transducer 2 and a dosing reservoir 3 from whose outlet 5 a micro droplet 6 can be delivered when the transducer 2 is activated. According to the invention, a carrier pad 9 is provided as a carrier material, comprising a drive device for retention and/or movement of the pad 9 in the form of a thread-shaped or bar-shaped actuating element 91 which can be moved through the dosing reservoir 3 of the dispenser 1 (direction of arrow). The carrier pad 9 is a continuous, sponge-like solid phase comprising an active surface which is as large as possible. The preferably porous material of the carrier pad 9, which material per se is incompressible, comprises for example nitrocellulose or a columnar filling material such as is used in HPLC separations (e.g. material "Poros" (registered trademark)).

Instead of the sample collection with the moved magnetic particles (first embodiment) a mechanical principle of operation is implemented in the second embodiment. The activation element 91 moves the carrier pad 9 through the interior space of the dosing reservoir 3 so as to collect sample molecules. The liquid 4 in the microdispenser 4 can flow through the carrier pad 9 so as to avoid any undesired delivery of liquid. After the enrichment process, when according to the function, the concentrated analyte molecules are delivered by the micro dispenser 1 to a particular substrate, the carrier pad 9 is pulled through the dispenser tip upward through the transducer 2.

For use in the processing of extremely small substance quantities, according to the invention, a dosing device is prepared by taking up the solid carrier material in the reservoir of the dosing device. In the first embodiment, taking up and depositing the magnetic particles in the reservoir (e.g. in the dosing reservoir of the microdispenser) takes place in that a particle suspension is filled into the reservoir either by way of the outlet of the reservoir or by an additional supply line and simultaneous influence of the magnetic field forces. As a result of the action of the magnetic field forces, the particles are immediately pulled to a reservoir wall where they are retained (depositing). In the second embodiment, the preparation step comprises the supply of the carrier pad in the reservoir of the dosing device and a fixation of the actuating element used for this purpose, such that the carrier pad is positioned in the reservoir near the outlet of the reservoir.

After the preparation step, a solution or dispensation of the substance samples of interest is taken up. Such take-up takes place accordingly by way of an outlet of the dosing device or by an additional supply line.

In the following binding step, the forces acting on the respective carrier material are changed such that the carrier material moves through the solution or suspension which has been taken up, and is thus in contact with the surrounding moving solution or suspension. This results in the substance being bound to the carrier material. In the first embodiment, the magnetic field forces are changed such that the magnetic particles move from the original location of deposition to another part of the reservoir wall (e.g. to the opposite wall). In the second embodiment, the drive element (e.g. reference 91 in FIG. 2), is moved such that the carrier material establishes contact with the surrounding moving solution or suspension. Preferably the movement of the carrier material through the solution takes place periodically in a multitude of movement sequences. The speed and duration of the carrier material movement and thus of the binding step are selected depending on the application.

After binding the substance of interest to the carrier material, the liquid is delivered from the reservoir of the dosing device through the outlet or through a pipe leading away from the opposite (upper) end. Depending on the application, a further solution or suspension with the substance of interest or without a sample substance can be admitted. In the first case this results in an enrichment of the substance in the reservoir. Concentration first takes place in the bound state on the carrier materials. After repeated supply of sample solutions, by take up of a suitable elution in the reservoir, the bound substance is then given off to the liquid or suspension. After separation of the substance from the particles or from the carrier pad, the concentration of the elution is higher than the originally supplied solution. In the second case it can be provided for purification solution to be supplied with which a predetermined type of substance which during the previous binding step had unintentionally been bound to the carrier materials, is separated again. This corresponds to a purification or further selective substance selection. Subsequently, again the substance is separated from the carrier materials by means of a suitable elution.

With the use of suitable repetition and selected substances, the previously described processing steps comprising the sample binding and the sample concentration and/or purification can also be applied for micropreparative and microsynthetic purposes. Thus it is for example possible to collect and/or purify a first reaction partner in the reservoir, before joining it for reaction with a suitably collected and/or purified second reaction partner. This reaction can take place in the bound state on the carrier material or in the dissolved or suspended state in the reservoir or after dispensing on a substrate.

Following substance release from the carrier materials, dosing according to the application takes place with the dosing equipment, by delivering the concentrated or purified solution to a target substrate. In the described microdispenser for example this takes place by application-specific droplet delivery through the outlet.

In a sample substance treatment according to the invention for example peptides from a volume of the order of magnitude of 1 µl to 2 µl are bound to the surface of magnetic particles, subsequently purified with approx. 10 µl of rinsing liquid and eluted in a few 100 nl to 10 nl. From each eluate, several analyses are made with substance quantities selected depending on the application. To this effect for example approx. 0.1 nl to 1.0 nl per analysis is dispensed to a sample carrier.

Figure 4:
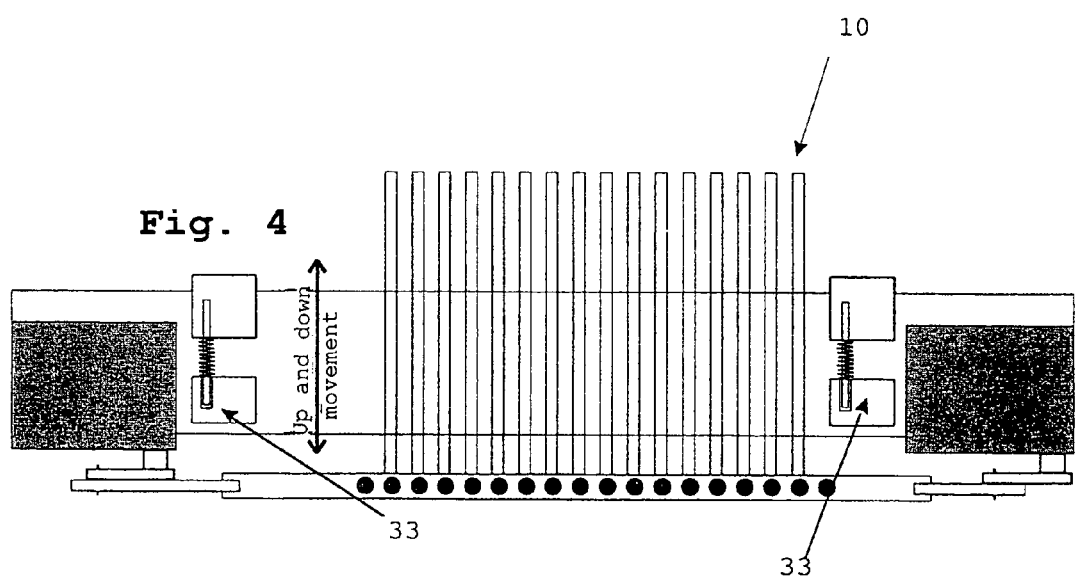
FIG. 4 is a diagrammatic side view of the device according to FIG. 3.

The following describes a further embodiment of the invention with a multitude of dosing devices in which substances can be processed according to the above-described principles, with reference to FIGS. 3 and 4.

FIGS. 3 and 4 diagrammatically show, in top view and side view respectively, a processing station for parallel processing of a multitude of substances. The processing station comprises a dispenser unit 10 with a multitude of microdispensers 1 (e.g. piezoelectric dispensers according to FIG. 1), a magnet unit 20 with a multitude of magnet devices 8 and a drive unit 30 which is equipped for adjusting the position or for moving the magnet unit 20 relative to the dispenser unit 10.

The microdispensers 1 of the dispenser unit 10 are arranged in a straight line. The number and distances of the microdispensers are selected depending on the application, from the shape of the respective macroscopic receptacle from which samples are to be taken. Preferably the arrangement of the microdispensers is matched to the shape of a micro titre plate. In the embodiment shown, for example sixteen microdispensers 1 are provided according to a micro titre plate with sixteen volumes arranged in rows. The microdispensers 1 are attached to a holding and servo device (not shown).

The magnet unit 20 comprises a multitude of magnet devices 8 whose number equals at least the number of microdispensers 1. Preferably at the end of the row of the microdispensers 1 an additional magnet unit is arranged to provide homogeneous field conditions in the microdispensers at the end of the row. Each magnet device 8 comprises two permanent magnets 81, 82, spaced apart, between each of which a microdispenser is arranged for substance processing.

The permanent magnets 81, 82 are attached to the longitudinal sides of a frame 21 enclosing the microdispenser row and extending longitudinally so as to correspond with the dispenser row. The frame 21 is movable with the drive unit 30 in a direction parallel to the longitudinal extension of the microdispenser 1 (up/down movement) and in a reference plane aligned perpendicularly to the microdispensers 1 (forward/reverse movement). The spacing of the longitudinal sides of the frame 21 is such that the magnetic particles of a microdispenser in a position immediately adjacent to one of the permanent magnets 81, 82, are essentially exposed exclusively to the field forces of this permanent magnet while they are exposed to negligible field forces of the opposite permanent magnet. In addition, the distance is selected such that during position change of the microdispensers from one permanent magnet to the opposite permanent magnet (forward/reverse movement) the particles, due to the effect of gravity, cannot sink far enough in the respective reservoir so as to leave the force effect range of the respective permanent magnet. This ensures that the particles do not reach the outlet and cannot cause any malfunctions at the outlet as a result of blockages or the like.

In the case of combination with microdispensers, the distance of the rows of permanent magnets along the longitudinal side of the frame 21 is less than 1 cm, preferably approx. 6 mm to 7.5 mm. The drive unit 30 comprises two servo motors 31 which are connected to the ends of the frame 21 via swivelling levers 32. By simultaneous activation of the servo motors 31 the frame 21 with the swivelling levers 32 can be swivelled from a first position in which the dispenser row is close to one of the permanent magnet rows (permanent magnets 81) to a second position in which the dispenser row is close to the respective other permanent magnet row (permanent magnets 82). Advantageously, all dispensers and all permanent magnets are moved simultaneously relative to each other. The servo motors are preferably equipped to provide different swivelling speeds. For example three swivelling speeds are provided with which different particle speeds in the reservoir of each microdispenser are achieved. With the three swivelling speeds, positioning change from the first to the second position for example takes approximately a quarter second, half a second and one and a half seconds respectively.

The drive unit 30 further comprises two servo devices 33 by means of which the height position of the magnet devices 8 is adjustable in relation to the longitudinal direction of the microdispensers. Preferably, the servo devices 33 are spring suspensions with predefined setting positions. Preferably a first position in which processing in the microdispensers takes place and a second position are provided in which the dispenser ends protrude below the plane of the frame 21 for example so as to be driven into a vessel (e.g. into the volume of a micro titre plate) for filling. To switch from the processing position to the filling position, the servo motors 31 with the frame 21 for release of the dispenser tips are pushed upward against return springs of the servo device 33 and anchored in the fill position. After filling, the anchoring is released and the return springs push the servo motors 31 with the frame 21 back into the processing position. Furthermore, the drive unit 30 comprises a motor suspension 34 whose operation is again synchronised with the holding and servo device of the dispenser row.

When implementing the above-mentioned second embodiment, the processing station according to FIGS. 3 and 4 has to be adapted. Accordingly, the carrier pads are to be attached in rows to a common carrier and are to be activated by means of matched actuating elements in one direction corresponding to the longitudinal direction of the microdispensers (up/down movement).

The actuating elements in particular comprise a wire or thread suspension for each carrier pad. By means of said wire or thread suspension the carrier pad can be drawn up from the outlet (or the nozzle) of the microdispenser to an upper dispenser region. Above the piezoelectric transducer, movement of the suspension can take place magnetically or mechanically.

Processing in microdispensers of extremely small substance quantities according to the invention has the advantage that only small quantities of elution agent are required to eluate the bound sample substances in the dispenser tip from the solid phase. For example 100 to 300 nl of a mixture of acetonitril (80% vol.) with trifluoroacetic acid (0.1% vol.) is used as an elution agent. Uptake of the elution agent is via the microdispenser outlet (nozzle), in that negative pressure (e.g. approx. 10 mbar) is generated at the microdispenser via a supply line. The elution agent is sucked into the microdispenser by way of setting the surface tension or the capillary forces.

Implementation of the invention is not limited to the embodiments described above. In particular the following modifications are possible. The simultaneous use of carrier material which can be magnetically and mechanically activated is possible. Instead of two permanent magnets it is possible to provide only one permanent magnet whose position in relation to the respective microdispenser with an adjustment device is changed such that the magnetic particles permanently remain under the influence of the magnetic field. It is also possible to provide more than two permanent magnets for each dispenser. Instead of the described microdispensers or micropipettes it is possible to use other dosing equipment. Additional means for forming the magnetic field in the region of the reservoir of the microdispensers can be provided. Instead of the permanent magnets, electromagnets or magnets based on microsuperconductors can be used, if there is sufficient space for their positioning. The steps described above of the method according to the invention can be repeated and modified so as to achieve particular processings.

What is claimed is:

1. A method for processing at least one substance in a reservoir of a microdosing device, said microdosing device being a micropipette or a microdispenser and said reservoir having an outlet being adapted for microdroplet delivery, comprising the steps of:
   arranging a solid carrier material as a solid phase with a binding-active surface in the reservoir, said carrier material being held with a drive device located outside said reservoir;
   collecting the substance in the reservoir by repeatedly performing the steps of uptaking a solution or suspension liquid with the substance into the reservoir, repeatedly moving the carrier material in the reservoir with said drive device and binding the substance to a surface of the carrier material and delivering the remaining liquid from the reservoir; and
   uptaking an elution agent separating the bound substance from the carrier material or a reaction partner reacting with the substance in the reservoir.

2. The method according to claim 1, further comprising moving the carrier material, which comprises magnetic particles, with a changeable magnetic field.

3. The method according to claim 2, wherein the changeable magnetic field is formed by simultaneous movement of permanent magnets in relation to the reservoir.

4. The method according to claim 2 in which the changeable magnetic field is generated by electromagnets or microsuperconductors.

5. The method according to claim 1, further comprising moving the carrier material, which comprises a carrier pad, with a mechanical actuating element.

6. The method according to claim 1, wherein the dosing device is a microdispenser or a micropipette.

7. The method according to claim 1, wherein processing the substance is selected from the group consisting of concentration, purification, preparation and synthetization.

8. The method according to claim 1, wherein the volume of the reservoir is less than 500 µl.

9. A device for processing at least one substance, comprising:
   a microdosing device having a reservoir in which a solid carrier material with a binding-active surface is movably arranged, the reservoir having a volume which is less than 10 µl and an outlet that delivers microdroplets in the sub-nl range, said microdosing device having a micropipette or a microdispenser; and
   a drive device located outside the reservoir for holding and multiply moving the carrier material in the reservoir, wherein
   the solid carrier material comprises magnetic particles and the drive device comprises two permanent magnets, between which the micropipette or the micro-dispenser is arranged, wherein the permanent magnets are spaced apart from each other and point with the same pole towards the reservoir and each of the permanent magnets has an adjustable spacing relative to the reservoir, and
   spacing of the two permanent magnets is such that the magnetic particles of the micropipette or the microdispener in a position immediately adjacent to one of the permanent magnets are essentially exposed exclusively to field forces of the one permanent magnet while they are exposed to negligible field forces of an opposite one of the permanent magnets, and that during position change of the micropipette or the microdispenser from one permanent magnet to the opposite permanent magnet the particles, due to the effect of gravity, cannot sink far enough in the reservoir to leave a force effect range of a respective one of the permanent magnets.

10. The device according to claim 9, further comprising a multitude of microdosing devices each having a reservoir, and a drive device comprising a multitude of magnet devices or carrier pads.

11. The device according to claim 10 in which the multitude of microdosing devices comprise a row of piezoelectric microdispensers.

\* \* \* \* \*